US008826912B2

(12) United States Patent  (10) Patent No.: US 8,826,912 B2
Bream, Jr.  (45) Date of Patent: Sep. 9, 2014

(54) SURGICAL DRAPE

(75) Inventor: Peter Reynolds Bream, Jr., Nashville, TN (US)

(73) Assignee: Vanderbilt University, Nashville, TN (US)

( * ) Notice: Subject to any disclaimer, the term of this patent is extended or adjusted under 35 U.S.C. 154(b) by 154 days.

(21) Appl. No.: 13/018,734

(22) Filed: Feb. 1, 2011

(65) Prior Publication Data

US 2011/0315150 A1   Dec. 29, 2011

Related U.S. Application Data

(60) Provisional application No. 61/358,568, filed on Jun. 25, 2010.

(51) Int. Cl.
 *A61B 19/08* (2006.01)
 *A61B 19/00* (2006.01)
(52) U.S. Cl.
 CPC .............. *A61B 19/08* (2013.01); *A61B 19/44* (2013.01); *A91B 2019/085* (2013.01)
 USPC ........................... 128/853; 128/849; 128/855
(58) Field of Classification Search
 USPC ......... 128/855, 853, 854, 849, 846, 851, 852, 128/850, 856
 See application file for complete search history.

(56) References Cited

U.S. PATENT DOCUMENTS

| | | | |
|---|---|---|---|
| 3,347,544 A | 10/1967 | Uffenorde | |
| 3,763,857 A | 10/1973 | Schrading | |
| 3,835,851 A | 9/1974 | Villari | |
| 4,122,848 A | 10/1978 | Carpel | |
| 4,231,119 A | 11/1980 | Quinn | |
| 4,321,917 A | 3/1982 | Campbell | |
| 4,336,797 A * | 6/1982 | Latucca et al. | 128/854 |
| D292,024 S | 9/1987 | Hanssen et al. | |
| 4,869,271 A | 9/1989 | Idris | |
| 4,976,274 A | 12/1990 | Hanssen | |
| 5,080,108 A * | 1/1992 | Roth | 128/849 |
| 5,140,996 A | 8/1992 | Sommers et al. | |
| 5,464,024 A | 11/1995 | Mills et al. | |
| D370,822 S | 6/1996 | Palomo et al. | |
| 5,640,975 A | 6/1997 | Diao | |
| 5,875,780 A | 3/1999 | Rodriguez | |
| 5,975,082 A | 11/1999 | Dowdy | |
| 6,032,670 A | 3/2000 | Miller | |
| 6,298,855 B1 | 10/2001 | Baird | |
| 6,345,622 B1 | 2/2002 | Chandler et al. | |
| 6,367,476 B1 | 4/2002 | Conn | |
| 6,405,730 B2 | 6/2002 | Levitt et al. | |
| 6,843,252 B2 | 1/2005 | Harrison et al. | |

(Continued)

*Primary Examiner* — Victoria J Hicks
(74) *Attorney, Agent, or Firm* — Welsh Flaxman & Gittler LLC

(57) ABSTRACT

A surgical drape includes a base sheet of thin, flexible material. The base sheet includes an upper surface, a lower surface, a first lateral side edge, a second lateral side edge, a top edge and a bottom edge. A first support member extends between the first lateral side edge and the top edge, and a second support member extends between the second lateral side edge and the top edge, the first and second support members being shaped and dimensioned to support the sheet in a tented configuration. The base sheet includes a first aperture formed therein and a second aperture formed therein. The first aperture and the second aperture are symmetrically positioned along opposite sides of the sheet relative to a central axis extending between the top edge and the bottom edge.

10 Claims, 7 Drawing Sheets

(56) References Cited

U.S. PATENT DOCUMENTS

| | | |
|---|---|---|
| 7,086,404 B2 | 8/2006 | Dusenbery et al. |
| 8,100,130 B2 * | 1/2012 | Allen et al. .................. 128/853 |
| 2003/0188753 A1 | 10/2003 | Jascomb |
| 2006/0169290 A1 * | 8/2006 | Harris et al. .................. 128/852 |
| 2007/0113859 A1 | 5/2007 | Allen et al. |
| 2007/0299302 A1 | 12/2007 | Small |
| 2009/0178685 A1 | 7/2009 | Haines et al. |
| 2010/0024831 A1 * | 2/2010 | Gustafsson et al. .......... 128/849 |

* cited by examiner

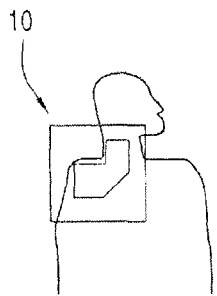 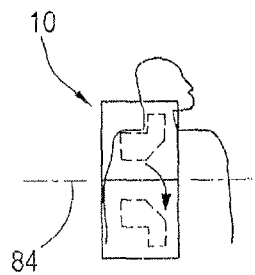 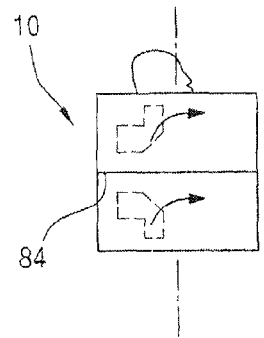
FIG. 8A  FIG. 8B  FIG. 8C
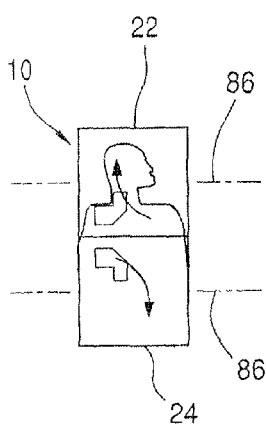 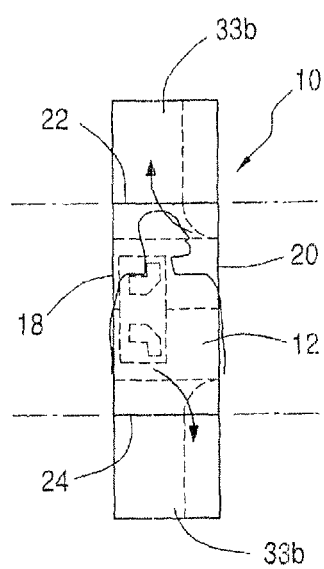 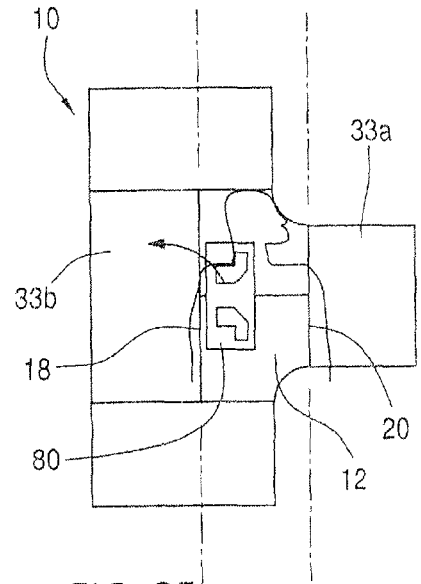
FIG. 8D  FIG. 8E  FIG. 8F
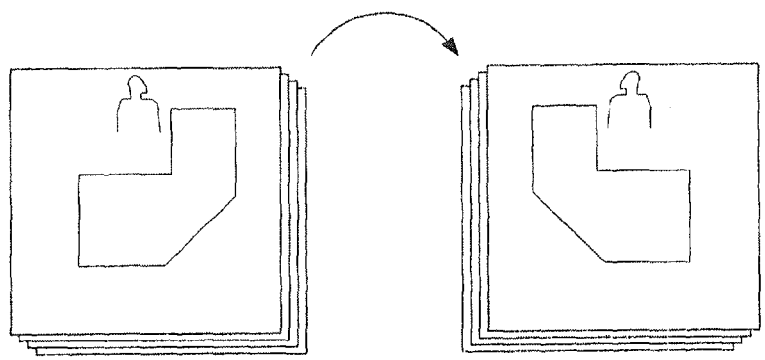
FIG. 8G

SURGICAL DRAPE

CROSS REFERENCE TO RELATED APPLICATION

This application claims the benefit of U.S. Provisional Patent Application Ser. No. 61/358,568, entitled "Surgical Drape", filed Jun. 25, 2010.

BACKGROUND OF THE INVENTION

1. Field of the Invention

The invention relates to a surgical drape. More particularly, the invention relates to a surgical drape for percutaneous procedures in the neck and upper chest.

2. Description of the Related Art

Maintenance of a sterile environment is critical to the safety of patients undergoing percutaneous procedures. This is accomplished by preparing the skin with appropriate bacteriocidal preparations (chlorohexidine gluconate or betadine) and then applying sterile drapes around the remaining unprepared areas. Many procedures performed by interventionalists require access to the veins of the neck and chest. The most common procedure is placement of a central venous catheter, where there is a special emphasis on maintaining absolute aseptic conditions to prevent catheter-related bloodstream infections. Unfortunately, this area is difficult to prepare and drape, due to the angle of the neck and upper chest, and close proximity to the face. There is not currently available a special sterile barrier designed for this area. Current practice is to arrange towels around the area to create a sterile barrier in this area and can require up to 10 sterile towels arranged around the area. However, maintaining the arrangement of the towels can be tenuous with a combative patient. As many procedures are done with local anesthesia or mild sedation, fully covering the face can lead to patient anxiety affecting the surgical procedure.

SUMMARY OF THE INVENTION

It is, therefore, an object of the present invention to provide a surgical drape including a base sheet of thin, flexible material. The base sheet includes an upper surface, a lower surface, a first lateral side edge, a second lateral side edge, a top edge and a bottom edge. A first support member extends between the first lateral side edge and the top edge, and a second support member extends between the second lateral side edge and the top edge, the first and second support members being shaped and dimensioned to support the sheet in a tented configuration. The base sheet includes a first aperture formed therein and a second aperture formed therein. The first aperture and the second aperture are symmetrically positioned along opposite sides of the sheet relative to a central axis extending between the top edge and the bottom edge. The first aperture is substantially L-shaped and includes a substantially rectangular first leg having a long axis and a short axis and a substantially rectangular second leg having a long axis and a short axis, wherein the long axis of the first leg is substantially perpendicular to the long axis of the second leg. The second aperture is substantially L-shaped and includes a substantially rectangular first leg having a long axis and a short axis and a substantially rectangular second leg having a long axis and a short axis, wherein the long axis of the first leg is substantially perpendicular to the long axis of the second leg.

It is also an object of the present invention to provide a surgical drape wherein the first support member is malleable and the second support member is malleable.

It is another object of the present invention to provide a surgical drape wherein the first support member is arcuate and the second support member is arcuate.

It is also an object of the present invention to provide a surgical drape including extension members secured to the base sheet.

It is another object of the present invention to provide a surgical drape wherein the extension members extend outwardly from the first lateral side edge, the second lateral side edge, the top edge and the bottom edge of the base sheet.

It is a further object of the present invention to provide a surgical drape including self adhesive tape selectively covering the first and second apertures.

It is another object of the present invention to provide a surgical drape including a plurality of fastening structures.

It is also an object of the present invention to provide a method for folding a surgical drape including a base sheet of thin, flexible material, the base sheet including an upper surface, a lower surface, a first lateral side edge, a second lateral side edge, a top edge and a bottom edge. The base sheet includes a first aperture formed therein and a second aperture formed therein. The first aperture and the second aperture are symmetrically positioned along opposite sides of the sheet relative to a central axis extending between the top edge and the bottom edge. The first and second extension members are secured to and extend from the base sheet. The method includes the following steps: laying the surgical drape flat upon a support surface with the base sheet and extension members fully extended; folding the first extension member about the second lateral side edge and the second extension member about the first lateral side edge; folding left and right sides of the second extension member about the top edge and the bottom edge of the base sheet to create a folded surgical drape including a halving bisecting line along a short axis of the folded surgical drape and quartering bisecting lines bisecting the folded surgical drape between the top and bottom edges of the base sheet; folding a portion of the folded surgical drape between the quartering bisecting lines and the top and bottom edges over the respective quartering bisecting lines; folding the surgical drape in half along a long axis of the folded surgical drape; and folding the surgical drape about the halving bisecting line.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 5 and 6 are respectively cross sectional views along the lines 5-5 and 6-6 in FIG. 1.

FIGS. 7A-7G and 8A-8G respectively disclose folding and unfolding of the surgical drape in accordance with the present invention.

DESCRIPTION OF THE PREFERRED EMBODIMENTS

Figure 1:
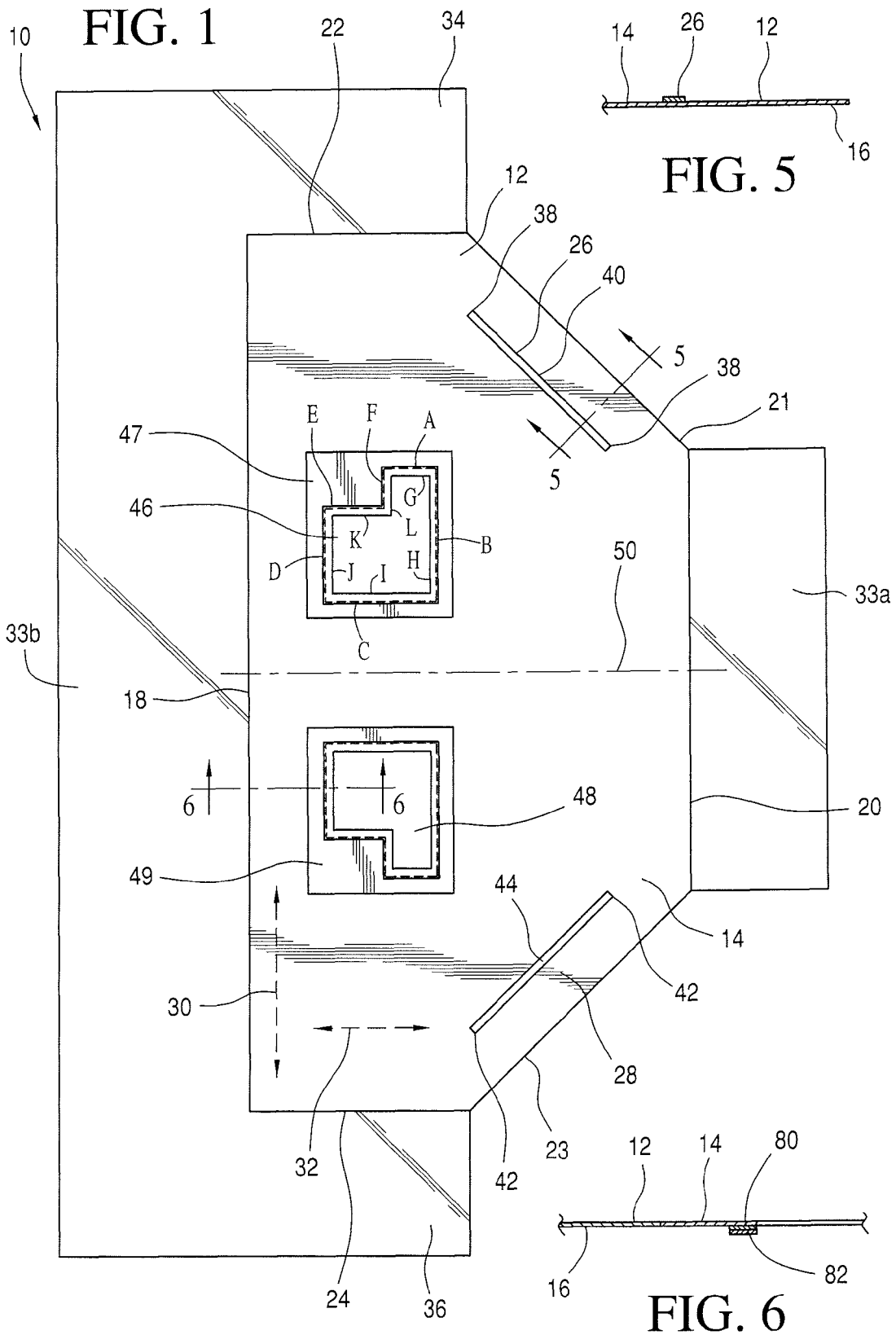
FIG. 1 is a top plan view of the present surgical drape.
Figure 2:
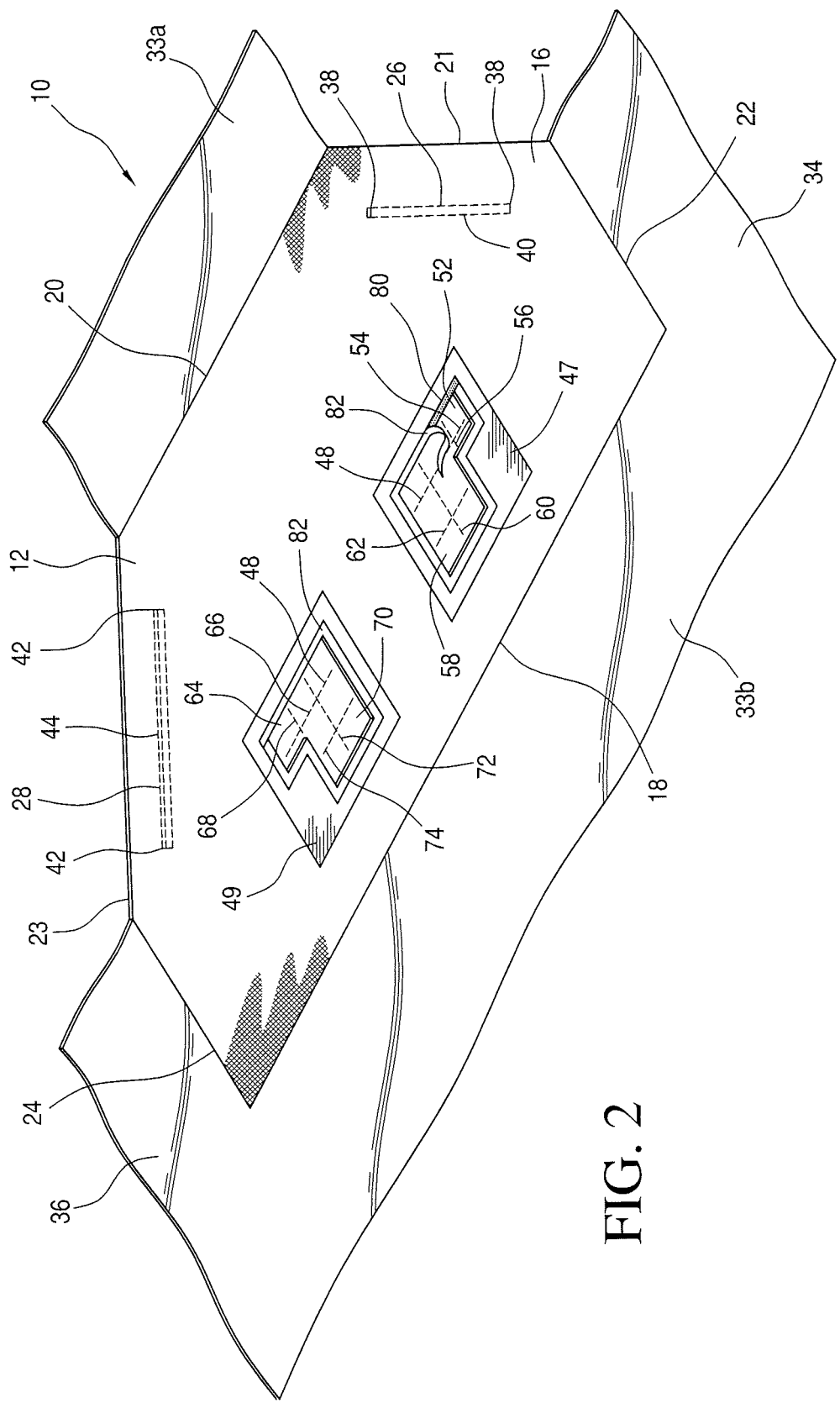
FIG. 2 is a perspective bottom view of the surgical drape shown in FIG. 1.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to FIGS. 1 to 6, the present chest and neck surgical drape 10 provides a simple one-step solution for creating a sterile barrier for percutaneous procedures in the neck and upper chest. It was designed by a physician with extensive experience in these procedures and, therefore, addresses the shortcomings of existing draping procedures. More particularly, the present surgical drape 10 allows for ready access to the internal jugular veins during tunneled catheter, subcutaneous chest port placement, or any other percutaneous procedure that utilizes access to this vein, regardless of whether access is achieved along the left or right side of the patient. In addition, there is equal access to the subclavian veins for the placement of central venous catheters, heart pacemakers, or any other procedure that requires access to these veins on either side.

The surgical drape 10 includes a base sheet 12 of thin, flexible material. The base sheet 12 includes an upper surface 14, a lower surface 16, a long first lateral side edge 18, a short second lateral side edge 20 that is shorter than the first lateral edge, a top edge 22 spaced from the second lateral side edge and a bottom edge 24 spaced from the second lateral side edge. An arcuate first support member 26 extends between the second lateral side edge 20 and the top edge 22 adjacent the top transition edge 21 (connecting the second lateral side edge 20 to the top edge 22, wherein the top transition edge 21 is oriented at an oblique angle relative to the second lateral side edge 20 and the to edge 22) of the base sheet 12 so as to define an arcuate cut-out between the second lateral side edge 20 and the top edge 22, and an arcuate second support member 28 extends between the second lateral side edge 20 and the bottom edge 24 adjacent the bottom transition edge 23 (connecting the second lateral side edge 20 to the bottom edge 24, wherein the bottom transition edge 23 is oriented at an oblique angle relative to the second lateral side edge 20 and the bottom edge 24) of the base sheet 12 so as to define an arcuate cut-out between the second lateral side edge 20 and the bottom edge 24.

In accordance with a preferred embodiment, the arcuate first and second support members 26, 28 are secured to the upper surface 14 of the base sheet 12 via heat sealing techniques, bonding techniques or sonic welding (see FIG. 5). With this configuration in mind, the surgical drape 10 includes a long axis 30 (or longitudinal axis) which extends from the top edge 22 to the bottom edge 24 and a short axis 32 (or lateral axis) which extends from the first lateral side edge 18 to the second lateral side edge 20. Consequently, the long axis 30 extends substantially parallel to the long axis of the patient and the short axis 32 extends across the body of the patient.

The arcuate first and second support members 26, 28 are preferably malleable and provide significant clinical and patient advantages. The first and second support members 26, 28 are referenced herein as arcuate because they may be bent into an arcuate shape to create a tenting effect as shown with reference to FIGS. 3 and 4 and as discussed below in greater detail. With this in mind, the arcuate first and second support members 26, 28 are bendable allowing a medical practitioner to form the support member in any desired shape. Accordingly, it is appreciated the structure referred to above as arcuate first and second support members may be bent in the form of a "straight" support member, an "arcuate" support member, or some other configuration suiting the desires of the medical practitioner employing the present drape.

The base sheet 12 of the surgical drape 10 is preferably manufactured from readily available and commonly used sterile drape materials. In accordance with a preferred embodiment, the base sheet 12 is composed of SMS (spunbond-meltblown-spunbond), Polyolefins, Polyethelene Films and a combination of materials providing absorbent attributes. As will be discussed below in greater detail, the area 47, 49 surrounding first and second apertures 46, 48 of the surgical drape 10 is a thicker layer of material to lend support. Although a preferred material is disclosed in accordance with a preferred embodiment of the present invention, it is contemplated the surgical drape 10 could be manufactured from a variety of materials without departing from the spirit of the present invention.

Figure 9:
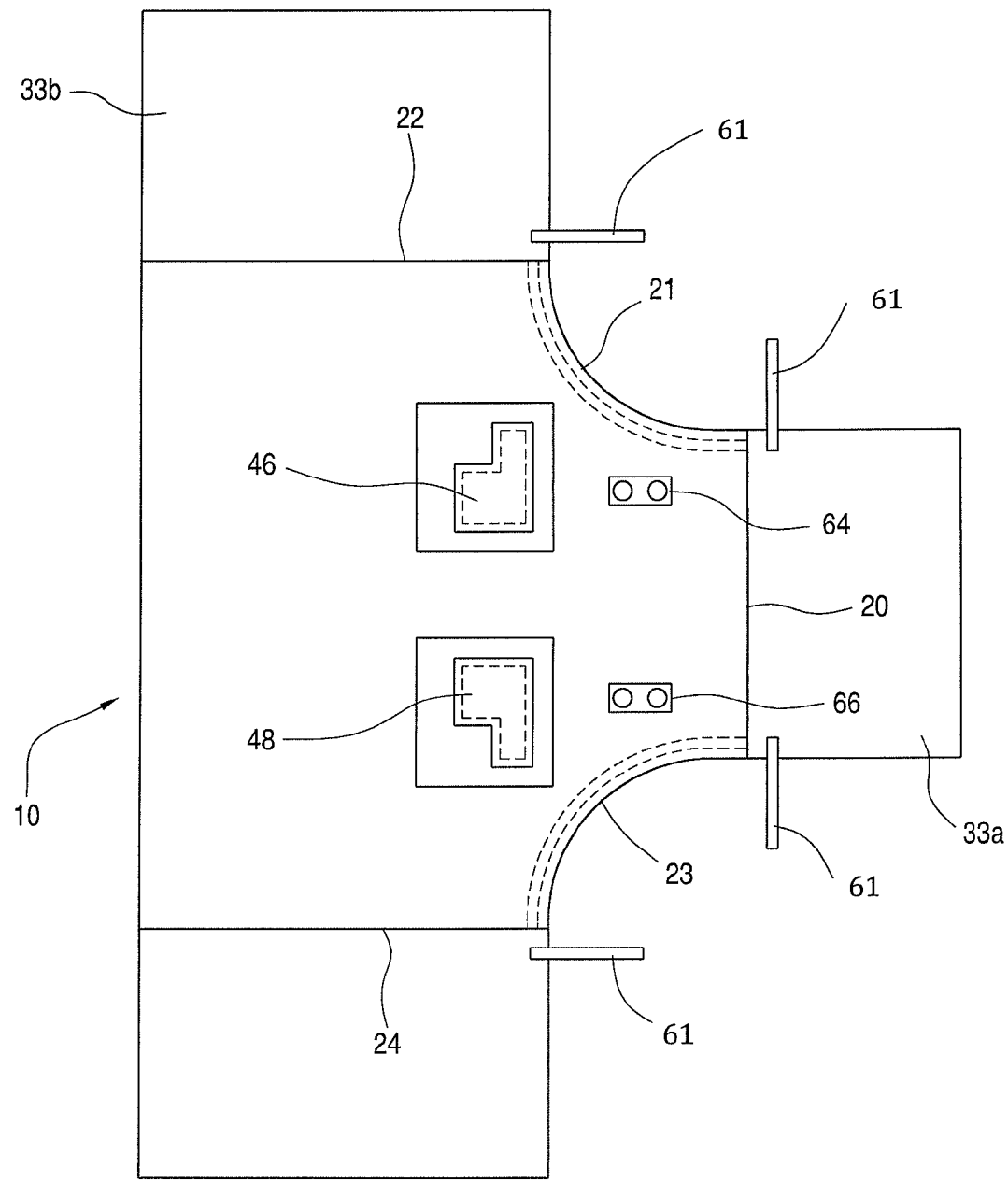
FIG. 9 is a top plan view in accordance with an alternate embodiment.

As discussed above, the base sheet 12 includes an upper surface 14, a lower surface 16, a first lateral side edge 18, a second lateral side edge 20, a top transition edge 21, a top edge 22, a bottom transition edge 23 and a bottom edge 24. With reference to FIG. 1, dimensions, in particular, with reference to the first and second apertures 46, 48 discussed below, are preferably as follows: A=10.2 cm; B=29.2 cm; C=20.3 cm; D=17.8 cm; E=10.2 cm; F=11.4 cm; G=6.2 cm; H=25.2 cm; I=16.3 cm; J=13.8 cm; K=8.2 cm; and L=9.4 cm. Other preferred dimensions include a first lateral side edge 18 of 180.3 cm, a second lateral side edge 20 of 86.4 cm, a top transition edge 21 of 63.64 cm, a top edge 22 of 45 cm, a bottom transition edge 23 of 63.64 cm and a bottom edge 24 of 45 cm, and wherein the distance from the first lateral side edge 18 to the second lateral side edge 20 is 90 cm. The dimensions of the alternate embodiment shown with reference to FIG. 9 are preferably as follows: A=10.2 cm; B=29.2 cm; C=20.3 cm; D=17.8 cm; E=10.2 cm; F=11.4 cm; G=6.2 cm; H=25.2 cm; I=16.3 cm; J=13.8 cm; K=8.2 cm; and L=9.4 cm. Other preferred dimensions include a first lateral side edge 18 of 180.3 cm, a second lateral side edge 20 of 86.4 cm, a top edge 22 of 43.2 cm and a bottom edge 24 of 43.2 cm, and wherein the distance from the first lateral side edge 18 to the second lateral side edge 20 is 90 cm. Although preferred dimensions are disclosed herein, it is contemplated the dimensions may be varied to suit patients of different sizes and anatomical characteristics, although the basic shape would remain the same.

In an effort to cover more of the patient's upper body, clear plastic extension members are secured to the base sheet 12 such that the extension members 33a, 33b extend outwardly from the first lateral side edge 18, the second lateral side edge 20, the top edge 22 and the bottom edge 24 (for a distance of 45 cm relative to the first lateral side edge 18 and the second lateral side edge 20 in accordance with a preferred embodiment, and for a distance of 30 cm relative to the top edge 22 and the bottom edge 24 in accordance with a preferred embodiment). As such, the extension members 33a, 33b expand the cover provided by the base sheet 12 all of the way around the surgical drape 10 with the exception of the top transition edge 21 where the first arcuate support member 26 is positioned and the bottom transition edge 23 where the second arcuate support member 28 is positioned.

Figure 3:
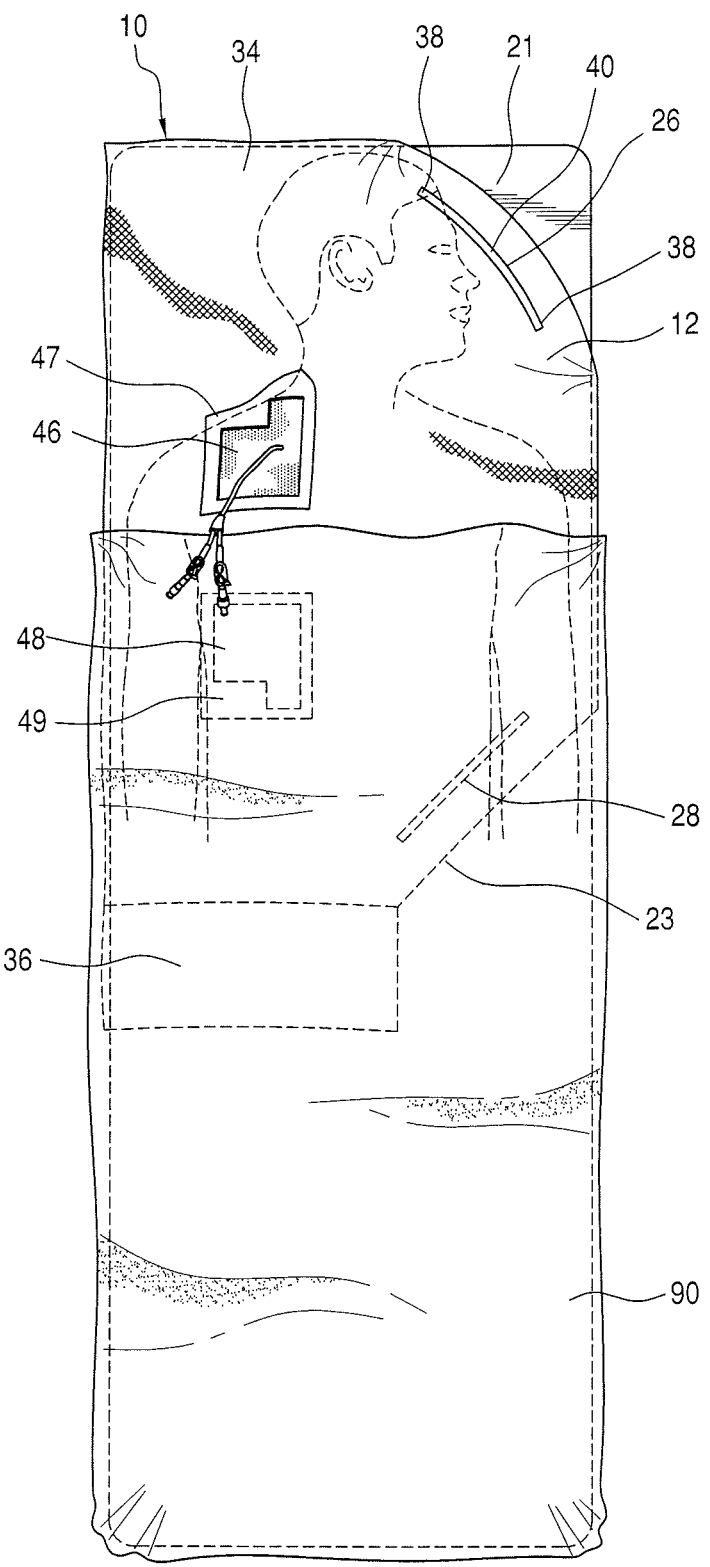
FIGS. 3 and 4 respectively show a side view and a top perspective view of the surgical drape in use with patients respectively lying with the head turned to the left and right.
Figure 4:
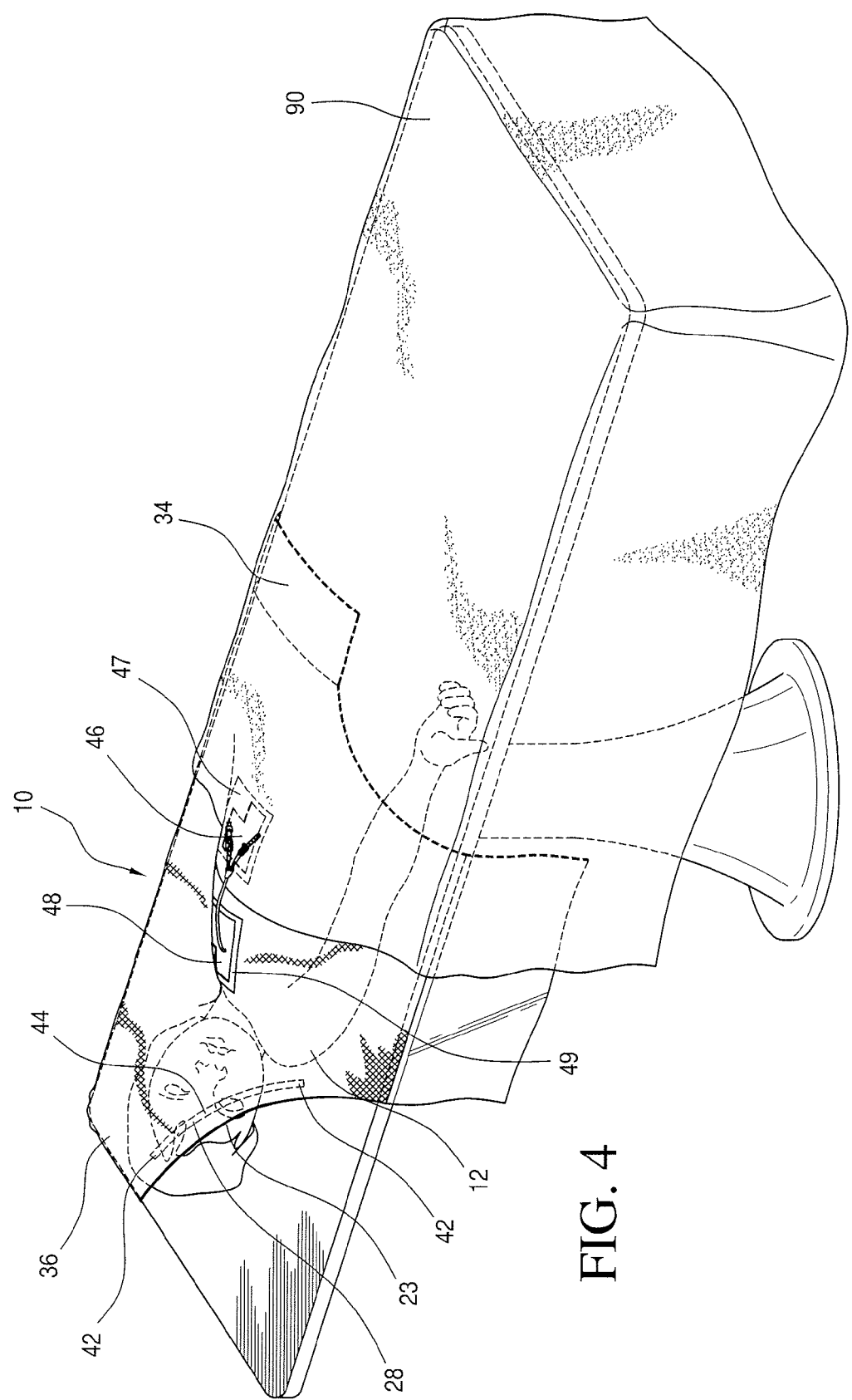

Although the top transition edge 21 and the bottom transition edge 23 are shown as straight edges in FIGS. 1, 2, 3 and 4, it is contemplated they may be structured as curved edges as shown with reference to the embodiment disclosed in FIG. 9. Further, and with regard to the embodiment shown in FIG. 9, the surgical drape 10 is provided with a fastening structure 61 allowing the surgical drape 10 to be secured to the surgical table. In accordance with a preferred embodiment, the bottom surface of the extension member 33b adjacent the top and bottom edges 22, 24 of the surgical drape 10 is provided with adhesive tape, hook and look fasteners (i.e., Velcro), or some other fastening structure 61. Also, fastening structures 61 as mentioned above are preferably provided on opposite sides of the extension member 33a adjacent the second lateral side edge 20. In practice, the surgical drape 10 is shaped and dimensioned for placement of either the top end 34, that is, the portion of the surgical drape 10 adjacent the top edge 22 thereof, or the bottom end 36, that is, the portion of the surgical drape 10 adjacent the bottom edge 24, over the head of the patient with the remainder of the surgical drape 10 positioned over the patient in a manner covering the upper body of the patient. The remainder of the patient's body is covered with standard blue surgical drapes 90 as shown in FIGS. 3 and 4. This conforms to the maximal sterile barrier as mandated by the CDC (Center for Disease Control) for sterile procedures. As such, it is desired to space the top end 34 of the surgical drape 10 or the bottom end 36 of the surgical drape 10 from the face of the patient. The first and second arcuate support members 26, 28 are, therefore, shaped and dimensioned to support the base sheet 12 in a tented configuration in the area adjacent to the face of the patient.

With this in mind, and with the patient lying supine on the surgical table, the surgical drape 10 is positioned over the patient with either the top end 34 or the bottom end 36 positioned so as to cover the face of the patient (for reasons as will be discussed below in greater detail). The head of the patient is then rotated to face either the first or the second arcuate support member 26, 28. Because the arcuate first and second support members 26, 28 are shaped and dimensioned to create a tenting configuration, the portion of the base sheet 12 supported thereby is lifted from the surface of the surgical table and away from the patient. As such, the face of the patient is spaced from the drape allowing for free access to the patient's face during the medical procedure. This tenting also allows patients under conscious sedation to breathe more easily and to decrease the potential for claustrophobia.

As briefly discussed above, the first arcuate support member 26 extends between the second lateral side edge 20 and the top edge 22, and parallel to the top transition edge 21, defining a concave recess therebetween (when bent for use as shown with reference to FIG. 3). The arcuate first support member 26 is shaped so as to define a quarter arc with the ends 38 of the arcuate first support member 26 sitting upon a support surface or the body of the patient and the central portion 40 of the arc being supported in an elevated position spaced from the support surface (see FIG. 3). Similarly, the arcuate second support member 28 extends between the second lateral side edge 20 and the bottom edge 24, and parallel to the bottom transition edge 23, defining a concave recess therebetween. The arcuate second support member 28 is shaped so as to define a quarter arc with the ends 42 of the arcuate second support member 28 sitting upon a support surface or the body of the patient and the central portion 44 of the arc being supported in an elevated position spaced from the support surface (see FIG. 4).

In accordance with a preferred embodiment, the arcuate first and second support members 26, 28 are manufactured from a formable or malleable metal. Although a formable metal is disclosed in accordance with a preferred embodiment of the present invention, it is contemplated other metal materials may be used without departing from the spirit of the present invention.

The arcuate first and second support members 26, 28 are shaped and dimensioned so that they may be oriented about the face of a patient so as to create a space between the drape and the face of the patient. As such, it is contemplated that, although an arcuate support member is disclosed in accordance with a preferred embodiment, a variety of similar shapes (for example, curved or straight) may be employed without departing from the spirit of the present invention.

In addition to the provision of the arcuate first and second support members 26, 28 positioned for allowing access to the face of the patient, the base sheet 12 includes a first aperture 46 formed therein adjacent the top end 34 of the surgical drape 10 and a second aperture 48 formed therein adjacent the bottom end of the surgical drape 10. The first aperture 46 and the second aperture 48 are symmetrically positioned along opposite sides of the base sheet 12 relative to a central axis 50 extending from the first lateral side edge 18 and the second lateral side edge 20, and bisecting the surgical drape 10 between the top edge 22 and the bottom edge 24 thereof.

The first aperture 46 is substantially L-shaped and includes a substantially rectangular first leg 52 having a long axis 54 and a short axis 56 and a substantially rectangular second leg 58 having a long axis 60 and a short axis 62. The long axis 54 of the first leg 52 is substantially perpendicular to the long axis 60 of the second leg 58. The second aperture 48 is substantially L-shaped and includes a substantially rectangular first leg 64 having a long axis 66 and a short axis 68 and a substantially rectangular second leg 70 having a long axis 72 and a short axis 74. The long axis 66 of the first leg 64 is substantially perpendicular to the long axis 72 of the second leg 70.

The first and second apertures 46, 48 are mirror images. That is, the base sheet 12 includes a central axis extending between the top edge 22 and the bottom edge 24 thereof and bisecting the base sheet 12. The first aperture 46 and the second aperture 48 are symmetrically positioned along opposite sides of the base sheet 12 relative to a central axis. As a result, if one were to fold the base sheet 12 along the central axis, the first aperture 46 would overlay the second aperture 48.

In accordance with a preferred embodiment, the dimensions of the first leg 52 and the second leg 58 of the first aperture 46 are as shown with reference to FIG. 1 and discussed above. Although preferred dimensions are disclosed herein, it is contemplated the dimensions may be varied to suit patients of different sizes and anatomical characteristics.

As a result of the symmetrical nature of the first and second apertures 46, 48 and the arcuate first and second support members 26, 28, the present surgical drape 10 is designed for use in conjunction with either right or left percutaneous procedures. Where access to the right side is desired, the top end 34 of the surgical drape 10 is placed over the head of the patient. The patient's head is oriented in a leftward facing orientation (when viewed from the patient's point of view). As a result, the first aperture 46 is ideally positioned for access to the subclavian vein and any adjunctive procedures such as pocket formation or tunnel formation. Where, however, left sided access is desired, the bottom end 36 of the surgical drape 10 is placed over the head of the patient. The patient's head is oriented in a rightward facing orientation (when viewed from the patient's point of view). As a result, the second aperture 48 is ideally positioned for the desired procedure.

The use of the present surgical drape 10 for both right and left sided procedures is facilitated by covering the edges along the lower surface 1.6 of the base sheet 12 which, surround the respective first and second apertures 46, 48 with self adhesive tape 80 (covered with paper backing 82 that may be removed to reveal either the first or second aperture 46, 48 depending upon whether a right or left sided access is desired).

Referring to the embodiment shown with reference to FIG. 9, the surgical drape 10 is further provided with first and second ultrasound cord holding tabs 64, 66 located between the respective first and second apertures 46, 48, and the short second lateral side edge 20. These tabs 64, 66 are structured and positioned in a manner facilitating usefulness for those medical practitioners employing the present surgical drape.

The present surgical drape 10 provides variety of advantages. Included among the advantages are: (1) a single drape can be used on the left or right side; (2) the unique shape of the aperture is specifically designed for procedures that utilize the neck and upper chest veins for access; (3) integrated tape ensures a tight seal around the prepared area; (4) the portion of the drape covering the face of the patient can be "tented" to reduce the feeling of claustrophobia and to allow for adequate air circulation; (5) can be packaged with existing sterile packs or available separate as an add-on; and (6) eliminates the use of multiple towels. Combined together, these advantages translate into shorter preparation times, greater confidence in the sterile barrier created and enhanced patient comfort and safety.

In addition to the utility offered by the surgical drape 10 disclosed above, folding (and unfolding) of the present surgical drape 10 offers advantages over previously existing surgical drapes. In particular, the folding pattern of the surgical drape 10 becomes part of the sterile draping process. By having a uniform way to unfold the surgical drape 10, you ensure that the area that you have just prepped remains sterile. The manner in which the present surgical drape 10 is folded requires that paper backing 82 be on the adhesive tape 80 surrounding the first and second apertures 46, 48. The medical practitioner will arrange the surgical drape 10 so that the left or right side is going to be used and tear off the paper backing 82 accordingly. Then the medical practitioner will press the adhesive tape 80 down onto the patient and start unfolding from that spot in a slowly expanding pattern. In this way, the surgical drape 10 secures the sterile area and uncovers it last.

Figure 7A:
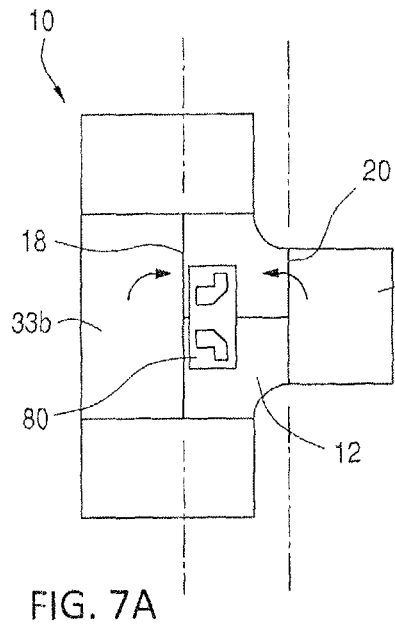

In practice, and with reference to FIGS. 7A-7G, the surgical drape 10 is laid flat upon a support surface with base sheet 12 and extension members 33a, 33b fully extended. Thereafter, extension member 33a is folded about the short second lateral side edge 20 and the extension member 33b is folded about the long first lateral side edge 18. Both extension members 33a, 33b are folded toward the center of the base sheet 12 in an overlapping configuration. Ultimately, and as will be appreciated based upon the following disclosure regarding unfolding of the surgical drape 10, it does not matter which extension member 33a, 33b is positioned on top of the other extension member 33a, 33b (Step 1 as shown in FIG. 7A).

Figure 7B:
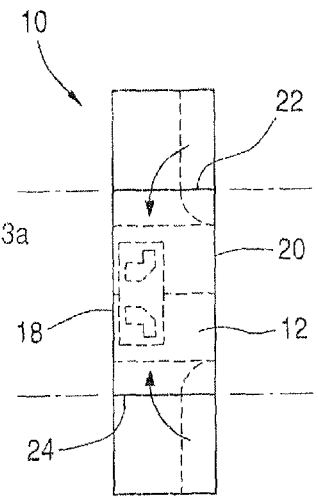

With the extensions members 33a and 33b folded along the first and second lateral side edges 18, 20, the unfolded left and right sides of the extension member 33b are folded about the top edge 22 and the bottom edge 24 of the base sheet 12. As discussed above, which portion of the extension member 33a, 33b lies over the other extension member 33a, 33b does not ultimately matter. The surgical drape 10 is now in a rectangular configuration with a long axis and a short axis (Step 2 as shown in FIG. 7B).

Figure 7C:
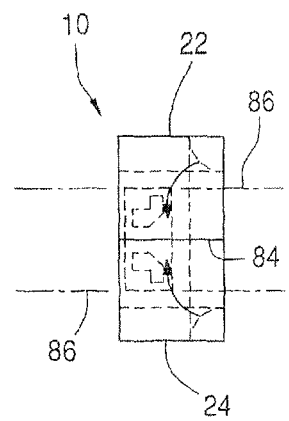
Figure 7D:
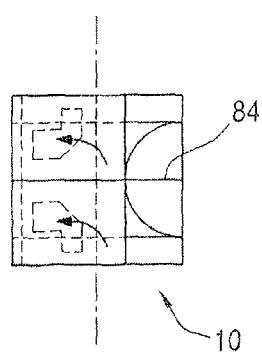
Figure 7E:
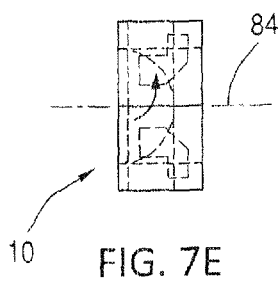
Figure 7F:
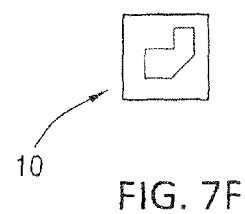
Figure 7G:
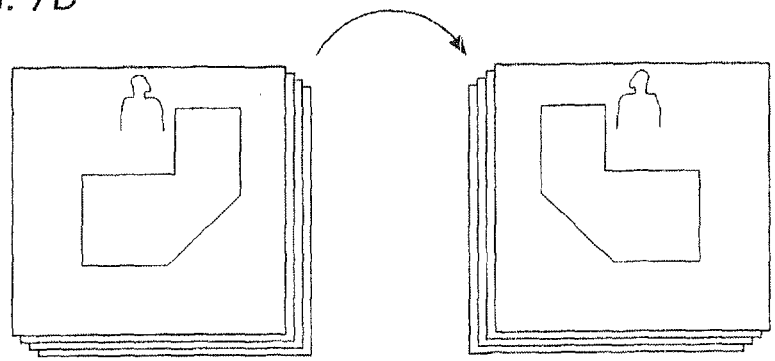

Viewing the folded surgical drape 10 in its rectangular configuration, it includes a halving bisecting line 84 along the short axis of the folded surgical drape 10, and quartering bisecting lines 86 bisecting the folded surgical drape 10 between the top and bottom edges 22, 24 of the base sheet 12 and the halving bisecting line 84, the surgical drape 10 is first folded such that the portion of the surgical drape 10 between the quartering bisecting lines 86 and the top and bottom edges 22, 24 of the folded surgical drape 10 are folded over the respective quartering bisecting lines 86 (Step 3 as shown in FIG. 7C). The surgical drape 10 is then folded in half along the long axis of the surgical drape as discussed above (that is, the axis perpendicular to the axis of the halving and quartering bisecting lines 84, 86) (Step 4 as shown in FIG. 7D). Thereafter, the surgical drape 10 is folded about the halving bisecting line 84 (Step 5 as shown in FIG. 7E). In this configuration, the paper backing 82 is exposed and the medical practitioner may simply flip over the folded surgical drape 10 to expose the proper orientation of either a head left position or a head right position (Step 6 as shown in FIG. 7F).

Turning now to FIGS. 8A-8G, once the head position is determined, the paper backing is removed and the medical practitioner will press the exposed adhesive down onto the patient and start unfolding from that spot in a slowly expanding pattern (Step 1 as shown in FIG. 8A). With reference to the example shown in FIG. 6, the head right position has been selected. The surgical drape is first unfolded about the halving bisecting line 84 (Step 2 as shown in FIG. 8B). The surgical drape 10 is then further opened by unfolded it about the long axis of the surgical drape as discussed above (that is, the axis perpendicular to the axis of the halving and quartering bisecting lines 84, 86) (Step 3 as shown in FIG. 8C). The surgical drape is then unfolded about the quartering bisecting lines 86, followed by unfolding about the top edge 22 and the bottom edge 24 of the base sheet 12 to reveal the left and right sides of the extension member 33b (Steps 4 and 5 as respectively shown in FIG. 8D & 8E). Finally, the extension members 33a, 33b are fully revealed by unfolding about the first and second lateral side edges 18, 20 (Step 6 as shown in FIG. 8F).

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A surgical drape, comprising:
a base sheet of thin, flexible material, the base sheet including an upper surface, a lower surface, a first lateral side edge, a second lateral side edge that is shorter than the first lateral side edge, a top edge spaced from the second lateral side edge and a bottom edge spaced from the second lateral side edge, as well as a top transition edge connecting the second lateral side edge to the top edge, the top transition edge being oriented at an oblique angle relative to the second lateral side edge and the top edge, and a bottom transition edge connecting the second lateral side edge to the bottom edge, the bottom transition edge being oriented at an oblique angle relative to the second lateral side edge and the bottom edge, wherein the top transition edge is a straight edge or a curved edge and the bottom transition edge is a straight edge or a curved edge; and
a malleable first support member adjacent to the top transition edge and extending from the second lateral side edge to the top edge, and a malleable second support member adjacent to the bottom transition edge and extending from the second lateral side edge to the bottom edge, the first and second support members being shaped and dimensioned to support the sheet in a tented configuration whereby in use the malleable first support member is capable of being shaped so as to define a quarter arc with ends of the malleable first support member adapted to sit upon a support surface or a body of a patient with a central portion of the quarter arc supported in an elevated position spaced from the support surface or the malleable second support member is capable of being shaped so as to define a quarter arc with ends of the malleable second support member adapted to sit upon the support surface or the body of the patient with a central portion of the quarter arc supported in an elevated position spaced from the support surface to thereby support a portion of the base sheet adjacent either the top transition edge or the bottom transition edge such that the base sheet adjacent either the top transition edge or the bottom transition edge is capable of being lifted from a surface of a surgical table and away from the patient in an area adjacent a face of the patient;

the base sheet including a first aperture formed therein and a second aperture formed therein; the first aperture and the second aperture being symmetrically positioned along opposite sides of the base sheet relative to a central axis extending between the top edge and the bottom edge;

the first aperture being substantially L-shaped and including a substantially rectangular first aperture first leg having a first aperture first leg long axis and a first aperture first leg short axis and a substantially rectangular first aperture second leg having a first aperture second leg long axis and a first aperture second leg short axis, wherein the first aperture first leg long axis is substantially perpendicular to the first aperture second leg long axis;

the second aperture being substantially L-shaped and including a substantially rectangular second aperture first leg having a second aperture first leg long axis and a second aperture first leg short axis and a substantially rectangular second aperture second leg having a second aperture second leg long axis and a second aperture second leg short axis, wherein the second aperture first leg long axis is substantially perpendicular to the second aperture second leg long axis.

2. The surgical drape according to claim 1, further including extension members secured to the base sheet.

3. The surgical drape according to claim 2, wherein the extension members extend outwardly from the first lateral side edge, the second lateral side edge, the top edge and the bottom edge of the base sheet.

4. The surgical drape according to claim 1, wherein the top transition edge is a curved edge and the bottom transition edge is a curved edge.

5. The surgical drape according to claim 4, wherein the first lateral side edge is 180.3 cm, the second lateral side edge is 86.4 cm, the top edge is 43.2 cm and the bottom edge is 43.2 cm, and wherein a distance from the first lateral side edge to the second lateral side edge is 90 cm.

6. The surgical drape according to claim 1, wherein the top transition edge is a straight edge and the bottom transition edge is a straight edge.

7. The surgical drape according to claim 6, wherein the first lateral side edge is 180.3 cm, the second lateral side edge is 86.4 cm, the top transition edge is 63.64 cm, the top edge is 45 cm, the bottom transition edge is 63.64 cm and the bottom edge is 45 cm, and wherein a distance from the first lateral side edge to the second lateral side edge is 90 cm.

8. The surgical drape according to claim 1, wherein the malleable first support member is arcuate or straight and the malleable second support member is arcuate or straight.

9. The surgical drape according to claim 1, further including self adhesive tape surrounding the first and second apertures.

10. The surgical drape according to claim 1, further including a plurality of fastening structures.

* * * * *